US009140790B2

(12) United States Patent
Hyun

(10) Patent No.: US 9,140,790 B2
(45) Date of Patent: Sep. 22, 2015

(54) ULTRASOUND SYSTEM AND METHOD OF FORMING ULTRASOUND IMAGE

(75) Inventor: Dong Gyu Hyun, Seoul (KR)

(73) Assignee: SAMSUNG MEDISON CO., LTD., Hongcheon-Gun, Gangwon-Do (KR)

( * ) Notice: Subject to any disclaimer, the term of this patent is extended or adjusted under 35 U.S.C. 154(b) by 962 days.

(21) Appl. No.: 12/204,659

(22) Filed: Sep. 4, 2008

(65) Prior Publication Data

US 2009/0062653 A1 Mar. 5, 2009

(30) Foreign Application Priority Data

Sep. 4, 2007 (KR) ........................ 10-2007-0089241

(51) Int. Cl.
*A61B 8/00* (2006.01)
*G01S 15/89* (2006.01)
*A61B 8/06* (2006.01)
*A61B 8/13* (2006.01)
*G01S 7/52* (2006.01)

(52) U.S. Cl.
CPC ............... *G01S 15/8979* (2013.01); *A61B 8/06* (2013.01); *A61B 8/13* (2013.01); *G01S 7/52071* (2013.01); *G01S 15/8993* (2013.01)

(58) Field of Classification Search
CPC ............ A61B 8/02; A61B 8/06; A61B 8/461; A61B 8/463; A61B 8/465; A61B 8/466; A61B 8/0883; A61B 8/0891; A61B 8/13; A61B 8/5246; A61B 8/488; A61B 8/5223; A61B 5/4887; G01S 7/52068; G01S 7/52071; G01S 15/8979; G01S 15/8993
See application file for complete search history.

(56) References Cited

U.S. PATENT DOCUMENTS

| 4,641,668 A | * | 2/1987 | Namekawa .................... 600/455 |
| 5,105,817 A | | 4/1992 | Uchibori et al. |

(Continued)

FOREIGN PATENT DOCUMENTS

| JP | 11-000327 A | 1/1999 |
| JP | 2008-100069 | 5/2008 |
| JP | 2008-194477 | 8/2008 |
| KR | 10-2007-0021420 | 2/2007 |

OTHER PUBLICATIONS

Jhang et al., 3-D Velocity Field Measurement Using Multiple Ultrasonic Plane Detections and High-Order Correlation Analysis, IEEE Transactions on Ultrasonics, Ferroelectrics, and Frequency Control, vol. 38, No. 2, Mar. 1991.*

(Continued)

*Primary Examiner* — Bo J Peng
(74) *Attorney, Agent, or Firm* — McDermott Will & Emery LLP

(57) ABSTRACT

The present invention relates to an ultrasound system and a method of forming an ultrasound image. The ultrasound system includes: a transmit/receive unit operable to transmit ultrasound signals to a target object and receive ultrasound echo signals to form receive signals based on the received ultrasound echo signals; a signal processing unit operable to form Doppler signals based on the receive signals; and an image processing unit operable to obtain information on a plurality of blood flow velocities at the target object from the Doppler signals, set a reference velocity, compute a dispersion of the plurality of the blood flow velocities with respect to the reference velocity, and form a 3-dimensional image indicating velocity changes at the respective locations in the target object by using the reference velocity and the dispersion.

3 Claims, 4 Drawing Sheets

(56) References Cited

U.S. PATENT DOCUMENTS

| | | | |
|---|---|---|---|
| 5,505,204 | A | 4/1996 | Picot et al. |
| 5,669,387 | A | 9/1997 | Mine |
| 6,210,168 | B1* | 4/2001 | Aiger et al. .................. 434/262 |
| 6,730,030 | B2* | 5/2004 | Palti .............................. 600/441 |
| 2003/0125624 | A1* | 7/2003 | Shiki ............................. 600/443 |
| 2005/0226482 | A1 | 10/2005 | Kuduvalli |
| 2008/0051661 | A1* | 2/2008 | Kataguchi et al. ............ 600/455 |
| 2008/0091106 | A1 | 4/2008 | Kim et al. |
| 2008/0194966 | A1 | 8/2008 | Kang |
| 2008/0306386 | A1* | 12/2008 | Baba et al. .................... 600/455 |

OTHER PUBLICATIONS

Goossen et al., Representation of Head-Centric Flow in the Human Motion Complex, The Journal of Neuroscience, May 24, 2006 • 26(21):5616-5627.*

Mottl-Link et al., Non-invasive assessment of differences between bileaflet and tilting-disc aortic valve prostheses by 3D-Doppler profiles, Interactive CardioVascular and Thoracic Surgery 4, 2005, 383-387.*

Matlab '2006, Matlab, The Language of Technical Computing, Graphics Version 7, Mar. 2006.*

Korean Office Action issued Korean Patent Application No. 10-2007-0089241, mailed Dec. 20, 2010.

Dubiel et al., "Betamethasone treatment and fetal lung perfusion evaluated with color Doppler energy imaging," Ultrasound Obstet. Gynecol., vol. 10, 1997, pp. 272-276.

Fenster et al., "3-D ultrasound imaging: a review," IEEE Engineering in Medicine and Biology, vol. 15, No. 6, Nov. 1, 1996, pp. 41-50.

Staalsen et al., "In vivo analysis and three-dimensional visualization of blood flow patterns at vascular end-to-side anastomoses," European Journal of Vascular and Endovascular Surgery, vol. 10, No. 2, Aug. 1, 1995, pp. 168-181.

Extended European Search Report for EP 08015527.8, mailed Jul. 28, 2009, 9 pages.

* cited by examiner

ULTRASOUND SYSTEM AND METHOD OF FORMING ULTRASOUND IMAGE

The present application claims priority from Korean Patent Application No. 10-2007-0089241 filed on Sep. 4, 2007, the entire subject matter of which is incorporated herein by reference.

BACKGROUND OF THE INVENTION

1. Technical Field

The present invention relates to an ultrasound system and a method of forming an ultrasound image.

2. Background Art

An ultrasound system has become an important and popular diagnostic tool due to its non-invasive and non-destructive nature. Modern high-performance ultrasound imaging diagnostic systems and techniques are commonly used to produce two- or three-dimensional images of internal features of patients.

Generally, the ultrasound system includes a probe, a beam former, a signal processing unit, an image processing unit and a display unit. The probe, which transmits and receives ultrasound signals, contains a plurality of transducer elements for reciprocally converting the ultrasound signals and the electrical signals. Each of the transducer elements in the probe may individually generate an ultrasound signal or several transducer elements may generate ultrasound signals at the same time. The ultrasound signals may be reflected from discrete planes (i.e., surfaces of reflectors) of acoustic impedance in the target object. The transducer elements may be operable to convert the received ultrasound echo signals into electrical receive signals. The beam former may be configured to apply delays to the electrical receive signal by considering positions between focal points and respective transducer elements to form a receive-focused beam. The signal processing unit performs analog-to-digital conversion, amplification and signal processing upon the receive-focused beam. The image processing unit may be operable to form an ultrasound image based on the signals outputted from the signal processing unit. The display unit may be configured to display the ultrasound image.

The Doppler effect is used in the ultrasound system to provide a color flow image showing velocity information of reflectors in the target object. The color flow image not only provides real-time blood flow visualization, but it can also accurately delineate a wide range of blood flow conditions, ranging from high velocities in large vessels to minute trickles coursing through small vessels.

The conventional ultrasound image may merely provide a color flow image showing velocity information of reflectors in the target object without indicating any velocity changes of the reflectors in the target object. Thus, it is difficult for the user to intuitively recognize the velocity change of the reflectors in the target object.

DETAILED DESCRIPTION OF THE INVENTION

Figure 1:
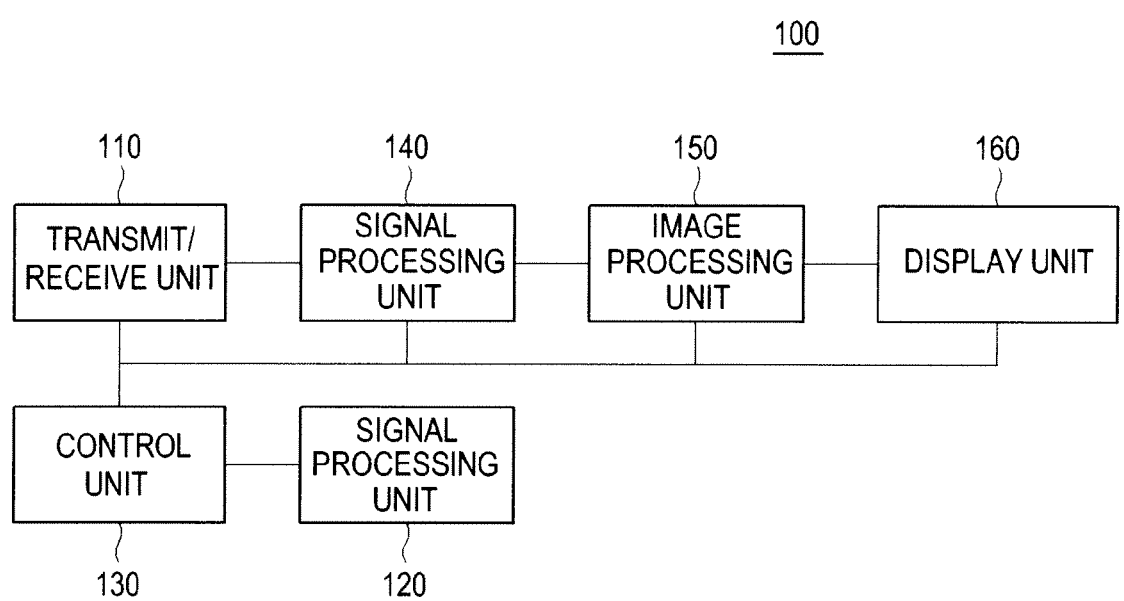
FIG. 1 is a block diagram showing an illustrative embodiment of an ultrasound system.

FIG. 1 is block diagram showing an ultrasound system constructed in accordance with one embodiment of the present invention. As shown in FIG. 1, the ultrasound system 100 includes a transmit/receive unit 110, an input unit 120, a control unit 130, a signal processing unit 140, an image processing unit 150 and a display unit 160.

The transmit/receive unit 110 may be operable to transmit ultrasound signals to a target object and receive ultrasound echo signals reflected from a target object under the control of the control unit 130. The transmit/receive unit 110 may include a probe (not shown) containing a plurality of transducer elements for reciprocally converting the ultrasound signals and the electric signals. The probe may be operable to convert the ultrasound echo signals into electrical receive signals. The transmit/receive unit 110 may further include a transmitter and a receiver. The transmitter may be operable to form a transmit pattern of transmit pulses, which are applied to transducer elements, such that the ultrasound signals generated from the transducer elements are focused on focal points. The receiver may be configured to perform receive focusing, i.e., apply delays to the receive signals in consideration of distances between the transducer elements and the focal points.

The input unit 120 may be operable to receive setup information from the user. The setup information may include information about an image mode of the ultrasound system 100 and information about location and size of a color box.

The control unit 130 may be configured to control the transmission and reception of the ultrasound signals in the transmit/receive unit 110 so that the transmit/receive unit 110 may obtain first receive signals for a B-mode image. If the setup information about the location and size of the color box is inputted, then the control unit 130 may be operable to control the transmission and reception of the ultrasound signals such that the transmit/receive unit 110 obtains second receive signals for a color flow image corresponding to the color box. The control unit 130 may be further operable to control operations of the signal processing unit 140, the image processing unit 150 and the display unit 160.

The signal processing unit 140 may be configured to perform signal processing upon the receive signals outputted from the transmit/receive unit 110 to desirable image signals. The signal processing unit 140 may perform signal processing upon the first receive signals to thereby form B-mode image signals. Also, the signal processing unit 140 may be operable to perform the signal processing upon the second receive signals to thereby form Doppler signals. The Doppler signals may be indicative of reflector velocities at a slice corresponding to the color box. The reflector velocities may be indicated in axial and lateral directions.

The image processing unit 150 may be configured to form the B-mode image based on the B-mode image signals. Further, the image processing unit 150 may obtain a plurality of reflector velocities based on the second image signals, set a reference velocity from the plurality of reflector velocities, and compute a dispersion of the plurality of reflector velocities. The image processing unit 150 may further form a 3-dimensional image three-dimensionally indicating velocity changes of the reflectors at the slice corresponding to the color box based on the reference velocity and the dispersion.

Figure 2:
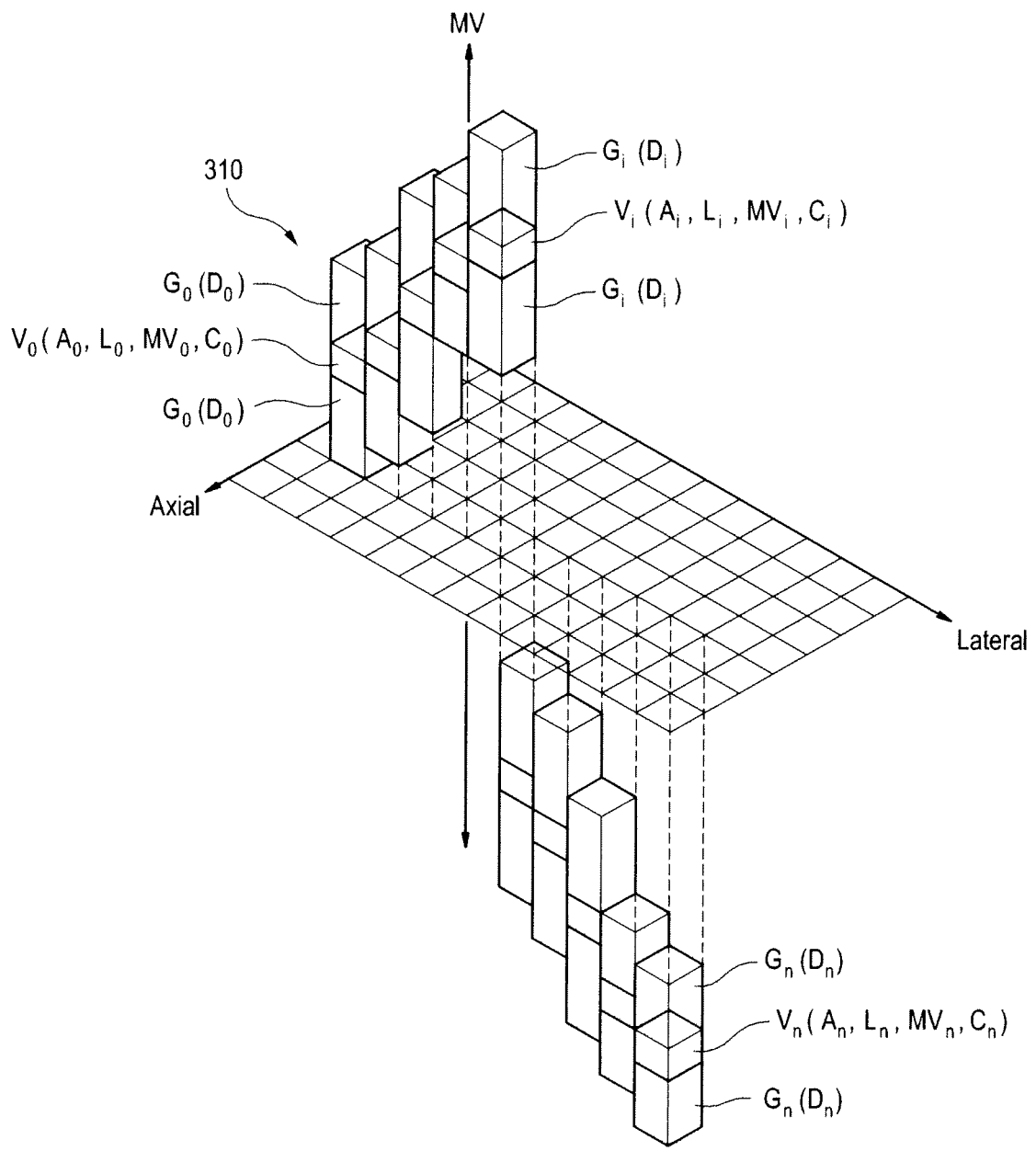
FIG. 2 is an exemplary diagram showing a 3-dimensional image indicating velocity changes at a target object in accordance with one embodiment of the present invention.
Figure 3:
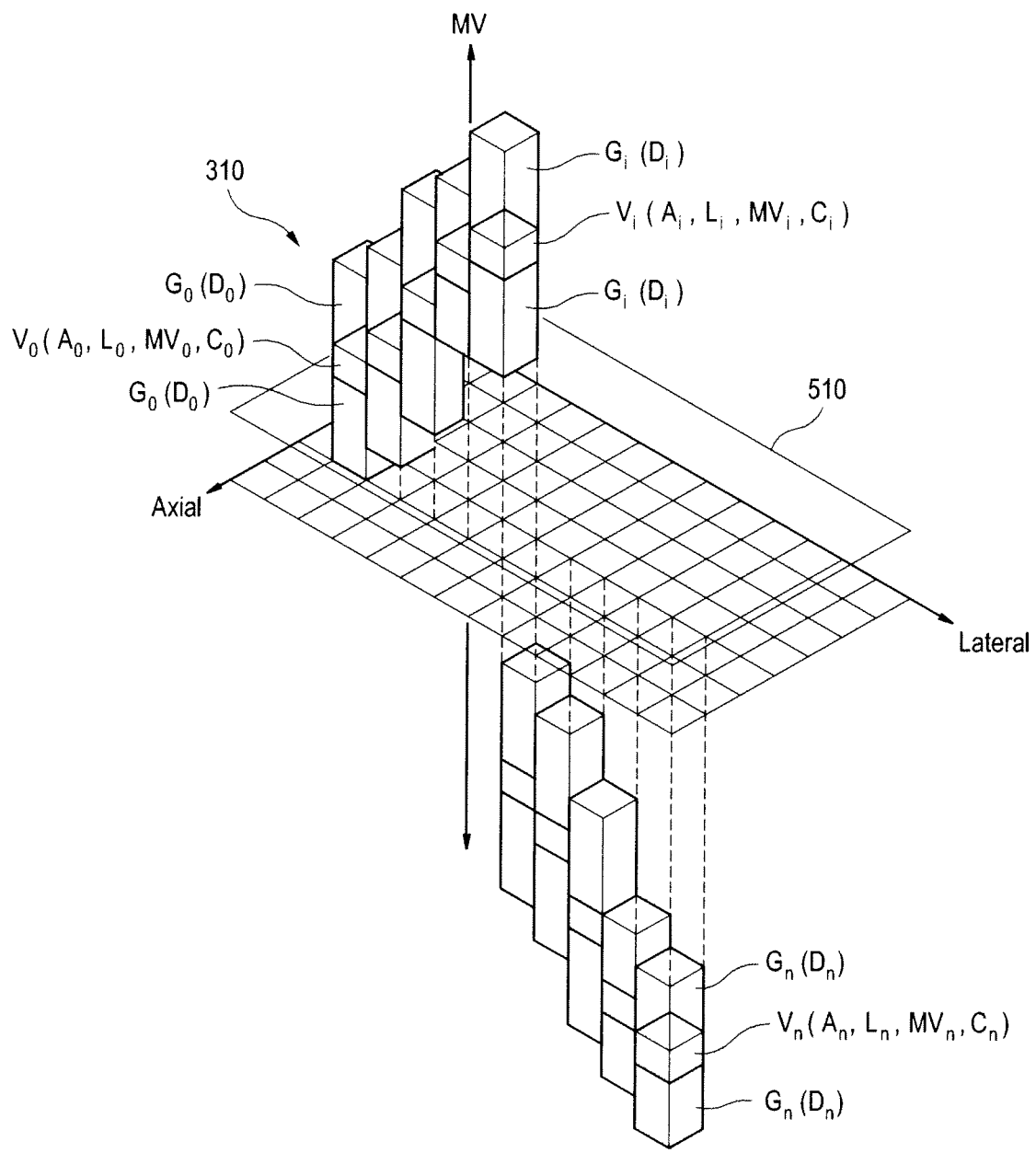
FIG. 3 is a diagram showing an example of a display where a B-mode image and a 3-dimensional image are displayed at the same time.

In accordance with one embodiment of the present invention, the image processing unit 150 may set a reference blood flow velocity from a plurality of blood flow velocities in the axial and lateral directions, and compute a dispersion of the blood flow velocities and the reference velocity. In such a case, the reference blood flow velocity may be an average velocity or a peak velocity of the plurality of blood flow velocities. The image processing unit 150 may be operable to form a 3-dimensional image 310 constructed with a plurality of voxels $V_0$ to $V_n$, as illustrated in FIG. 2. Each of the voxels may be formed to indicate the reference velocity and the dispersion on a 3-dimensional space configured with an axial direction A, a lateral direction L and a reference velocity. Each of the voxels may be further indicative of a predetermined color C corresponding to the reference velocity.

The image processing unit 150 may form a 3-dimensional image 310 with a 3-dimensional graph in accordance with another embodiment of the present invention. The 3-dimensional graph may be constructed with a plurality of bars $G_0$ to $G_n$. The bars may be indicative of dispersions $D_0$ to $D_n$ with respect to the reference velocities MV of the respective voxels $V_0$ to $V_n$. The image processing unit 150 may be operable to compute the average velocity from a plurality of blood flow velocities and then compute dispersion with respect to the reference velocity. For example, when the blood flow velocities are 4 m/s, 8 m/s, 12 m/s and 16 m/s, the reference velocity may be 10 m/s, which is the average velocity thereof. Also, the dispersion may be 9 m/s with respect to the reference velocity of 10 m/s. The image processing unit 130 may be operable to form voxels based on the reference velocity of 10 m/s and a color corresponding to the reference color, and then form a 3-dimensional graph having a height corresponding to the dispersion (9 m/s) at top and bottom of the corresponding voxel along an axis of the reference velocity MV. Although the dispersion is indicated with the 3-dimensional graph in accordance with one embodiment of the present invention, it is certainly not limited thereto. It should be understood to a person skilled in the art that the dispersion can be indicated with various types.

The image processing unit 150 may be operable to perform perspective projection or orthographic projection upon the 3-dimensional image 310 to form a 3-dimensional projection image. The input unit 120 may be further operable to receive setup information of a reference plane 510 to be set in the 3-dimensional image 310. The image processing unit 150 may form a 2-dimensional image corresponding to the reference plane 510 based on the setup information.

Figure 4:
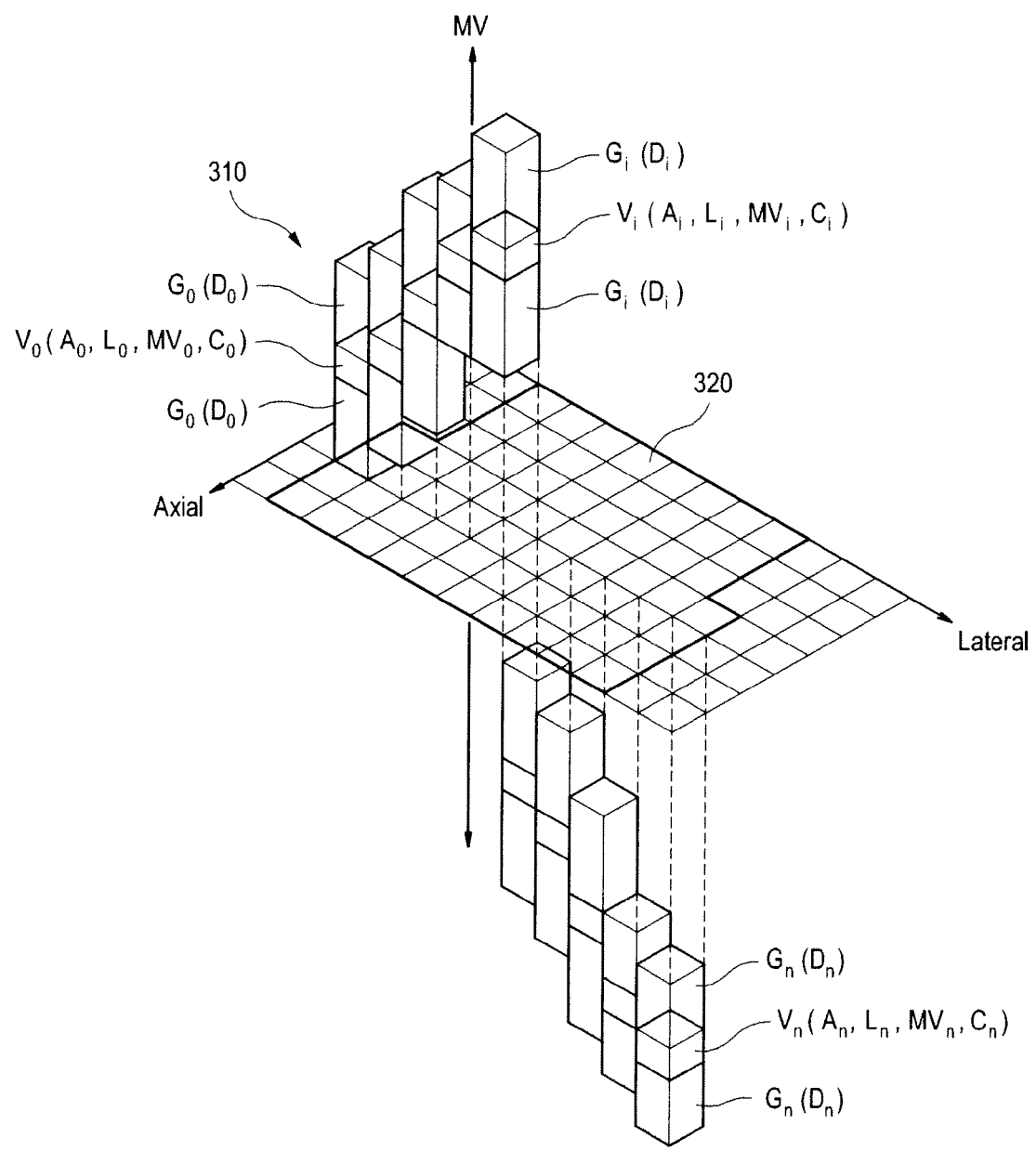
FIG. 4 is a diagram showing an example of a display where a reference plane is set on a 3-dimensional image in accordance with the present invention.

The display unit 160 may be operable to display the B-mode image, the 3-dimensional image and the 2-dimensional image. In accordance with one embodiment of the present invention, the display unit 160 may display only the 3-dimensional image. In accordance with another embodiment of the present invention, the display unit 160 may simultaneously display the B-mode image 320 and the 3-dimensional image 310, as shown in FIG. 4. In accordance with yet another embodiment of the present invention, the display unit 160 may display the B-mode image 320 and the 3-dimensional image 310 on different screen areas.

As mentioned above, since the present invention may provide a 3-dimensional image showing velocity changes of moving reflectors (e.g., blood flows) in the target object, it is helpful for the user to examine the target object through intuitive reorganization of the velocity changes.

In accordance with one embodiment of the present invention, there is provided an ultrasound system comprising: a transmit/receive unit operable to transmit ultrasound signals to a target object and receive ultrasound echo signals to form receive signals based on the received ultrasound echo signals; an signal processing unit operable to form Doppler signals based on the receive signals; and an image processing unit operable to obtain information on a plurality of blood flow velocities at the target object from the Doppler signals, set a reference velocity, compute a dispersion of the plurality of the blood flow velocities with respect to the reference velocity, and form a 3-dimensional image three-dimensionally indicating velocity changes at the respective locations in the target object by using the reference velocity and the dispersion.

In accordance with another embodiment of the present invention, there is provided a method of forming an ultrasound image, comprising: a) transmitting ultrasound signals to a target object to form receive signals based on ultrasound echo signals reflected from the target object: b) forming Doppler signals based on the receive signals; and c) obtaining a plurality of blood flow velocities from the Doppler signals, setting a reference velocity, computing a dispersion of the a plurality of the blood flow velocities and forming a 3-dimensional image three-dimensionally indicating velocity changes at the target object by using the reference velocity and the dispersion.

Any reference in this specification to "one embodiment," "an embodiment," "example embodiment," etc. means that a particular feature, structure or characteristic described in connection with the embodiment is included in at least one embodiment of the present invention. The appearances of such phrases in various places in the specification are not necessarily all referring to the same embodiment. Further, when a particular feature, structure or characteristic is described in connection with any embodiment, it is submitted that it is within the purview of one skilled in the art to effect such feature, structure or characteristic in connection with other ones of the embodiments.

Although embodiments have been described with reference to a number of illustrative embodiments thereof, it should be understood that numerous other modifications and embodiments can be devised by those skilled in the art that will fall within the spirit and scope of the principles of this disclosure. More particularly, numerous variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. An ultrasound system, comprising:
   a transmitter/receiver configured to transmit ultrasound signals to a target object and receiving ultrasound echo signals to form receive signals based on the received ultrasound echo signals;
   a signal processor configured to form Doppler signals for a color box set by setup information received by an input unit based on the receive signals and form B-mode image signals for a B-mode image of the target object based on the receive signals; and
   an image processor configured to obtain information on a plurality of blood flow velocities at a first region of a slice corresponding to the color box from the Doppler signals, set a reference velocity of the plurality of blood flow velocities, form a 3-dimensional image including a voxel indicative of the reference velocity in the first region and 3-dimensional graphs indicative of a dispersion of the plurality of the blood flow velocities with respect to the reference velocity, and display the 3-dimensional image with the B-mode image, wherein the voxel includes a x-coordinate value indicative of axial location of the first region, a y-coordinate value indicative of lateral location of the first region and a z-coordinate value indicative of the reference velocity of the first region, and the 3-dimensional graphs are formed at a top and a bottom of a corresponding voxel along a z-axis, and a color of the voxel is a color corresponding to the reference velocity, the 3-dimensional graphs having a height corresponding to the dispersion.

2. The ultrasound system of claim 1, wherein the input unit further receives setup information for setting a reference plane on the 3-dimensional image, wherein the image processor is configured to set the reference plane on the 3-dimensional image and form a 2-dimensional image corresponding to the reference plane.

3. The ultrasound system of claim 1, wherein the image processor is configured to perform a perspective projection upon the 3-dimensional image to form a 3-dimensional projection image.

* * * * *